United States Patent
Chen

(10) Patent No.: US 9,724,035 B2
(45) Date of Patent: Aug. 8, 2017

(54) IN VIVO VISUALIZATION OF LYMPHATIC TISSUE

(71) Applicant: The Regents of the University of California, Oakland, CA (US)

(72) Inventor: Lu Chen, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 109 days.

(21) Appl. No.: 14/069,116

(22) Filed: Oct. 31, 2013

(65) Prior Publication Data

US 2014/0121512 A1    May 1, 2014

Related U.S. Application Data

(60) Provisional application No. 61/720,764, filed on Oct. 31, 2012.

(51) Int. Cl.
*A61B 5/00*    (2006.01)

(52) U.S. Cl.
CPC ............ *A61B 5/414* (2013.01); *A61B 5/0071* (2013.01); *A61B 5/418* (2013.01); *A61B 2503/40* (2013.01)

(58) Field of Classification Search
None
See application file for complete search history.

(56) References Cited

PUBLICATIONS

Hoffmann et al. FITC-dextran for measuring apoplast pH and apoplastic pH gradients between various cell types in sunflower leaves. 1995 Physiol. Plant. 95: 327-335.*
Bock et al. Bevacizumab as a potent inhibitor of inflammatory corneal angiogenesis and lymphangiogenesis. 2007 Invest. Ophthalmol. Vis. Sci. 48: 2545-2552.*
McElroy et al. Fluorescent LYVE-1 antibody to image dynamically lymphatic trafficking of cancer cells in vivo. 2009 J. Surg. Res. 151: 68-73.*
Carrasco MA. Subconjunctival bevacizumab for corneal neovascularization in herpetic stromal keratitis. 2008 Cornea 27: 743-745.*
Davies et al. Increased retinal neovascularization in Fas ligand-deficient mice. 2003 Invest. Ophthalmol. Vis Sci. 44: 3202-3210.*
Alexander et al. Dynamic imaging of cancer growth and invasion: a modified skin-fold chamber model. 2008 Histochem. Cell Biol. 130: 1147-1154.*
Yuen et al. Live imaging of newly formed lymphatic vessels in the cornea. 2011 Cell. Res. 21: 1745-1749. Published online Nov. 15, 2011.*
Chen; et al. "Ocular Lymphatics: State-of-the-Art Review", Lymphology (Jun. 2009), 42(2):66-76.
Chen; et al. "Experimental Models to Study Lymphatic and Blood Vascular Metastasis", J Surg Oncol (May 2011), 103(6):475-483.
Chen; et al. "Vascular endothelial growth factor receptor-3 mediates induction of corneal alloimmunity", Nature Medicine (Aug. 2004), 10(8):813-815.
Cursiefen; et al. "Time Course of Angiogenesis and Lymphangiogenesis After Brief Corneal Inflammation", Cornea (May 2006), 25(4):443-447.
Ecoiffier; et al. "Conjunctival Lymphatic Response to Corneal Inflammation in Mice", Journal of Ophthalmology (2012), vol. 2012, Article ID 953187, pp. 1-6.
Gimbrone; et al. "Tumor Growth and Neovascularization: An Experimental Model Using the Rabbit Cornea", Journal of the National Cancer Institute (Feb. 1974), 52(2):413-427.
Grimaldo; et al. "Very Late Antigen-1 Mediates Corneal Lymphangiogenesis", Investigative Ophthalmolgy & Visual Science (Jun. 2011), 52(7):4808-4812.
Oliver; et al. "The rediscovery of the lymphatic system: old and new insights into the development and biological function of the lymphatic vasculature", Genes & Development (Apr. 2002), 16(7):773-783.
Ran; et al. "Macrophage-Mediated Lymphangiogenesis: The Emerging Role of Macrophages as Lymphatic Endothelial Progenitors", Cancers (Sep. 2012), 4(3):618-657.
Swartz; et al. "Transport in lymphatic capillaries. I. Macroscopic measurements using residence time distribution theory", American Physiological Society (Jan. 1996), 270(1Pt2):H324-H329.
Takakura; et al. "Enhanced Lymphatic Delivery of Mitomycin C Conjugated with Dextran", Cancer Research (Jun. 1984), 44(6):2505-2510.
Tammela; et al. "Lymphangiogenesis: Molecular Mechanisms and Future Promise", Cell (Feb. 2010), 140(4):460-476.
Truong; et al. "Novel Characterization of Lymphatic Valve Formation during Corneal Inflammation", PLoS One (2011), 6(7):e21918, pp. 1-6.
Zhang; et al. "Spontaneous Lymphatic Vessel Formation and Regression in the Murine Cornea", Investigative Ophthalmology & Visual Science (Jan. 2011), 52(1):334-338.

(Continued)

*Primary Examiner* — Michael G. Hartley
*Assistant Examiner* — Jennifer Lamberski
(74) *Attorney, Agent, or Firm* — Glenn J. Foulds; Bret E. Field; Bozicevic, Field & Francis LLP

(57) ABSTRACT

Aspects of the invention include methods for visualizing lymphatic tissue in an ocular region, e.g., the cornea, of a living subject, such as a mouse or human. In certain embodiments, the methods include contacting the region with a fluorescently-labeled lymphatic tissue-specific dye, e.g., FITC or rhodamine labeled dextran, and detecting the labeled dye to visualize lymphatic tissue in the region, where the visualization may vary, from an image obtained at a single time to a video over a period of time. The invention finds use in a variety of different applications, including research and therapeutic applications.

23 Claims, 3 Drawing Sheets

(56) References Cited

PUBLICATIONS

Steven et al. "Intravital Two-Photon Microscopy of Immune Cell Dynamics in Corneal Lymphatic Vessels", PLoS One, Oct. 2011, vol. 6, No. 10, e26253, 9 pages.

* cited by examiner

IN VIVO VISUALIZATION OF LYMPHATIC TISSUE

CROSS REFERENCE TO RELATED APPLICATIONS

This application claims priority to the filing date of U.S. Provisional Patent Application Ser. No. 61/720,764, filed on Oct. 31, 2012, the disclosure of which application is herein incorporated by reference in its entirety.

STATEMENT REGARDING FEDERALLY SPONSORED RESEARCH

This invention was made with government support under EY017392 awarded by the National Institutes of Health. The government has certain rights in the invention.

INTRODUCTION

Lymphatic vessel research represents an explosive field of new discovery in recent years. Compared to blood vessels which have been studied intensively in the past, lymphatic research has suffered centuries of ignorance due to the lack of a convenient method to identify lymphatic vessels. Unlike blood vessels, lymphatic vessels are not easily visible. Accompanying the blood circulation, the lymphatic network penetrates most tissues in the body and plays critical roles in a broad spectrum of functions, such as immune surveillance, body fluid regulation, and fat and vitamin absorption. Numerous diseases and conditions are therefore associated with lymphatic dysfunction, which include but are not limited to cancer metastasis, tissue and major organ (heart, kidney and lung) transplant rejection, inflammatory and immune diseases, infections, obesity, diabetes, AIDS, hypertension and lymphedema. These disorders can be disabling, disfiguring, and even life threatening. To date, there is still little effective treatment for lymphatic disorders, so it is a field with an urgent demand for new experimental approaches and therapeutic protocols. The burdens associated with lymphatic diseases are immense. For example, lymphedema (primary or secondary to cancer therapy) alone affects at least over 6 million individuals in the United States and more than 170 million people worldwide.

The cornea of the eye provides an ideal site for blood and lymphatic vessel research. As a unique transparent tissue in the body, it is naturally devoid of any vascular structures, blood or lymphatic. However, both vessel types are induced into the cornea after an inflammatory, infectious, traumatic, toxic or chemical damage event. Once induced, the lymphatic vessels facilitate high volume delivery of immune cells and accelerate inflammation and transplant rejection. Since there are no pre-existing or background vessels to consider, it is exceptionally easy and straightforward to assess a neo-vascular response in this tissue. Basically, any vascular structures detected in the cornea are newly formed, whether they pertain to a biological, pathological, or pharmacological stimulation or intervention. Results from corneal studies bear broad implications and can be readily applied to other research fields. As estimated by Judah Folkman, the grandfather of tumor angiogenesis research, more than one third of our basic knowledge on blood vessels is derived from studies with the cornea during past centuries. Indeed, the use of this tissue for tumor angiogenesis research dates back to 1970s. More recently, lymphatic research using the cornea has generated a considerable amount of promising data as well. For example, collective data from many researchers have demonstrated that lymphatic vessels, but not blood vessels, primarily mediate transplant rejection; transplant rejection can be inhibited by molecular blockade of the lymphatic pathway; and the cornea possesses a unique and full range of plasticity in lymphatic formation and regression. Studies on corneal lymphatic vessels and transplant rejection are important because lymphatic growth accompanies many corneal diseases, and the clinical burden of graft rejection in the lymphatic vessel-rich corneas is tremendous. As many as 50-90% of these grafts are rejected, irrespective of current treatment modalities. Corneal lymphatic research promises to provide potential novel therapeutic strategies for this condition.

Despite the recent advances in corneal lymphatic research, further in-depth investigation has been greatly hampered by serious technical limitations. For example, the conventional immunohistochemistry method which has been heavily relied upon to identify lymphatic vessels involves multiple steps of tissue fixation and antibody staining, which are both time consuming and labor intensive. Moreover, this method works with dead tissues and does not generate real time information on lymphatic vessels in the context of their natural morphology, state, or interaction with other components in the local living environment. Since the tissue is excised at a fixed time point, this method cannot be used for time-course study on the same tissue or subject for a certain period of time. Nevertheless, lymphangiogenesis (the development of new lymphatic vessels) is a dynamic and progressive process, and it is critical to obtain such longitudinal information for many studies, whether to track lymphatic changes from an early to a late stage, or to evaluate lymphatic responses to a biological or pharmaceutical intervention. Furthermore, it is also difficult to use the conventional method to study cell origins of lymphatic endothelial cells. When assays are performed on dead tissues, it is difficult to discern whether the cells detected on lymphatic vessels at one time point are merely in transit through the vascular wall, or are destined for long-term integration at their identified position.

SUMMARY

Aspects of the invention include methods for visualizing lymphatic tissue in a region, e.g., the cornea, of a living subject, such as a mouse or human. In certain embodiments, the methods include contacting the region with a fluorescently-labeled lymphatic tissue-specific dye, e.g., FITC or rhodamine labeled dextran, and detecting the labeled dye to visualize lymphatic tissue in the region, where the visualization may vary, from an image obtained at a single time to a video over a period of time. The invention finds use in a variety of different applications, including research and therapeutic applications.

In some embodiments, aspects of the invention include methods for visualizing lymphatic tissue in an ocular region, e.g., portion of an eye, of a living subject, the methods involving contacting the region with a detectably-labeled lymphatic tissue-specific dye, and detecting the labeled dye to visualize lymphatic tissue in the region. In some embodiments, the portion of the eye is the cornea. In certain embodiments, the methods involve inducing lymphangiogenesis in the cornea. In some embodiments, lymphangiogenesis is induced in the cornea using a suture protocol, an implantation protocol, or a transplantation protocol.

In some embodiments, the methods involve introducing the detectably-labeled lymphatic tissue-specific dye into a subconjunctival space. In some embodiments, the detectably-labeled lymphatic tissue-specific dye includes a fluorescent label covalently bound to a physiologically-acceptable polysaccharide. In some embodiments, the fluorescent label includes a physiologically-acceptable xanthene dye. In some embodiments, the xanthene dye is selected from the group including fluoresceins, eosins and rhodamines.

In some embodiments, the polysaccharide has a molecular weight ranging from 1,000 up to 10,000 kDa. In some embodiments, the physiologically-acceptable polysaccharide is dextran. In some embodiments, visualizing the lymphatic tissue involves obtaining an image at a single time. In some embodiments, visualizing the lymphatic tissue involves obtaining two or more images at different times. In some embodiments, visualizing the lymphatic tissue involves obtaining a video over a period of time.

In some embodiments, aspects of the invention include methods that further involve visualizing blood vessels in the portion of the subject's eye. In some embodiments, the methods further involve contacting the target region with a candidate agent and evaluating the impact of the candidate agent on lymphatic and/or blood vessel activity in the target region. In some embodiments, the candidate agent is covalently bound to the detectably-labeled lymphatic tissue-specific dye, e.g., to deliver the candidate agent directly to a lymphatic tissue in the subject's eye.

In some embodiments, the methods further involve contacting target region with a compound that includes detectably-labeled lymphatic tissue-specific dye conjugated to a therapeutic agent. In certain embodiments, the therapeutic agent is covalently bound to the detectably-labeled lymphatic tissue-specific dye to deliver the therapeutic agent directly to a target lymphatic tissue, e.g., in an ocular location.

In some embodiments, the methods further involve contacting the target region with a lymphatic tissue-specific antibody and detecting the antibody. In some embodiments, the detectably-labeled lymphatic tissue-specific dye includes a fluorescent label having a first color, and the lymphatic tissue-specific antibody comprises a fluorescent label having a second color that is different from the first color.

In some embodiments, the living subject is a mammal. In some embodiments, the mammal is a mouse. In some embodiments, the mammal is a human.

In some embodiments, aspects of the invention include systems for visualizing lymphatic tissue in a target region, e.g., ocular region, such as a portion of an eye, of a living subject, the systems including a detectably-labeled lymphatic tissue-specific dye, and a device for detecting a signal from the detectable label in the target location. In certain embodiments, the systems further include a lymphatic tissue-specific antibody.

DETAILED DESCRIPTION

Figure 1:
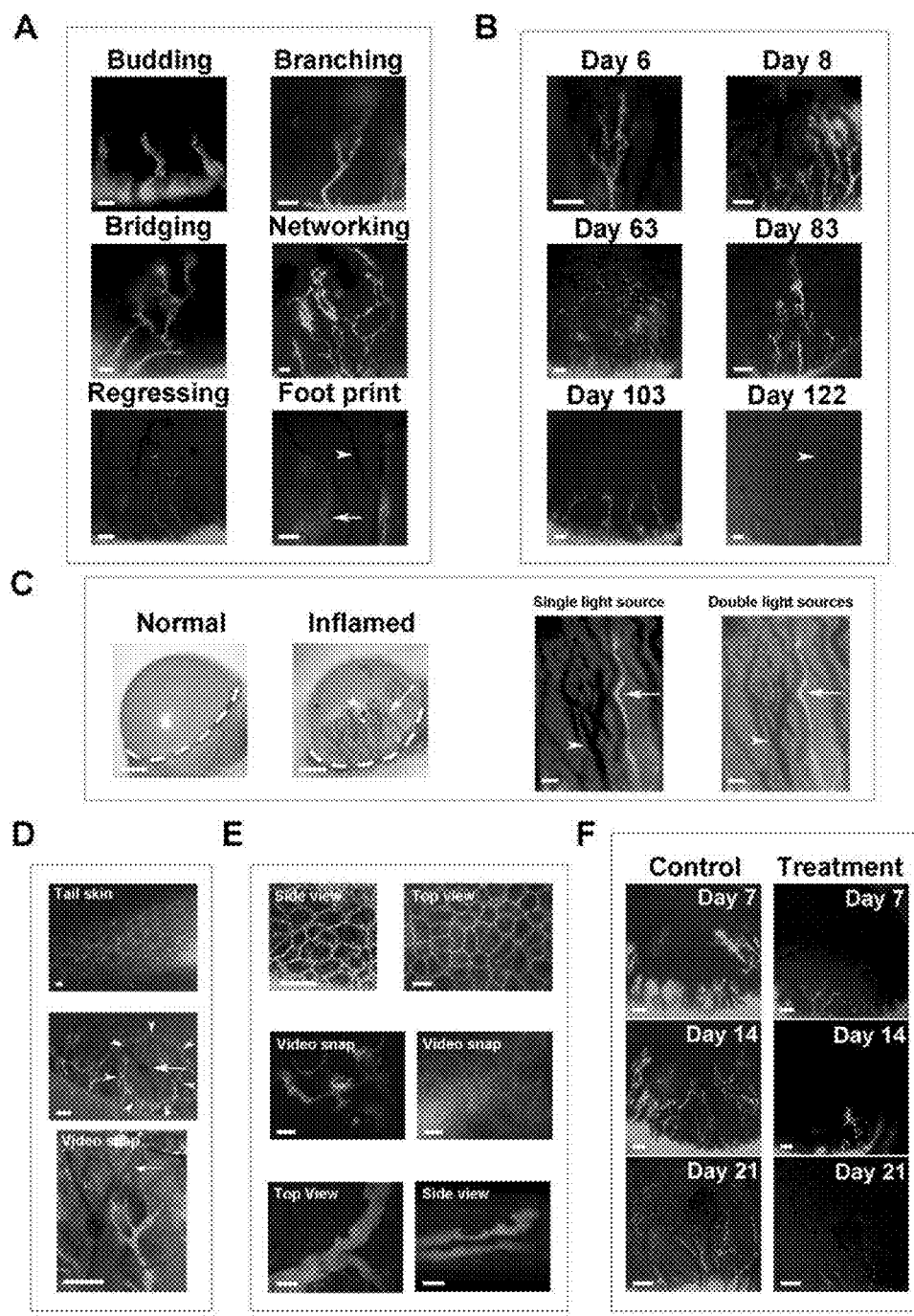
FIG. 1 illustrates live imaging of newly formed lymphatic vessels in an inflamed cornea. Panel A: Lymphatic vessels of various shapes and complexity. Arrow: foot prints of an almost regressed lymphatic vessel; Arrowhead: blood vessel. Panel B: Longitudinal tracking of dynamic lymphatic processes in the same corneas in the progression (top panels) or regression phase (middle and lower panels). Arrowhead: blood vessel. Panel C: Comparison between ophthalmic slit-lamp microscopy (left two panels; scale bars: 1000 µm) and imaging using the subject methods, which also reveals lymphatic vessels (right two panels) in the corneas 2 weeks after suture placement. Arrows: lymphatic vessels; Arrowheads: blood vessels. Panel D: Comparison between live imaging of lymphatic vessels in normal tail skin and inflamed cornea 2 weeks after suture placement. Top: cross-sectional view of background lymphatics in the skin. Middle: entire morphological tree of new lymphatic vessels in the cornea showing terminal lymphatics (arrowheads) encircling a suture spot (arrow). Lower: snap image taken from a video. Panel E: Live images showing ultra-structure of the cornea with lymphatic vessels. Top: side and top views of epithelial cells in layers. Middle: snap pictures showing lymphatic vessels in the stroma. Lower: snap pictures showing lymphatic vessels from different angel of view. Scale bars: 20 µm. Panel F: Real time in vivo evaluation of the effect of systemic VEGFR-2 blockade on corneal inflammatory lymphangiogenesis. Scale bars: 100 µm unless otherwise indicated.

As summarized above, aspects of the invention include methods for visualizing lymphatic tissue in a region, e.g., the cornea, of a living subject, such as a mouse or human. In certain embodiments, the methods include contacting the region with a fluorescently-labeled lymphatic tissue-specific dye, e.g., FITC or rhodamine labeled dextran, and detecting the labeled dye to visualize lymphatic tissue in the region, where the visualization may vary, from an image obtained at a single time to a video over a period of time. The invention finds use in a variety of different applications, including research and therapeutic applications.

Before the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges and are also encompassed within embodiments of the present disclosure, subject to any specifically excluded limit in the stated range. Where the stated range includes one or both of the limits, ranges excluding either or both of those included limits are also included in embodiments of the present disclosure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the invention include methods of visualizing lymphatic tissue in a living subject. By "visualizing lymphatic tissue" is meant creating one or more images of lymphatic tissue that can be viewed by an observer. In some instances, the methods involve contacting a region of a living subject with a lymphatic tissue-specific dye, and detecting the dye to visualize a lymphatic tissue while the subject is still alive. Lymphatic tissue-specific dyes in accordance with embodiments of the invention are compositions that bind to or associate with lymphatic tissue to a detectably greater extent than other tissue, such that lymphatic tissue can be distinguished from other tissue in a field of view. In some instances, lymphatic tissue-specific dyes in accordance with embodiments of the invention are compositions that preferentially bind to or associate with lymphatic tissue, e.g., lymphatic endothelial cells, and which do not substantially bind to or associate with other tissue types, e.g., vascular endothelium found in blood vessels. Accordingly, lymphatic tissue-specific dyes distinguish lymphatic tissue from other tissue types, and can be used to visualize lymphatic tissue in a subject.

Lymphatic tissue-specific dyes in accordance with embodiments of the invention are generally physiologically-acceptable polysaccharides whose molecular structure imparts the ability to preferentially bind to or associate with lymphatic tissue. In some embodiments, the polysaccharide has a molecular weight ranging from about 1,000, up to about 2,000, up to about 3,000, up to about 4,000, up to about 5,000, up to about 6,000, up to about 7,000, up to about 8,000, up to about 9,000, or up to about 10,000 kDa or more. In some instances, the polysaccharide component has a weight ranging from 1000 to 20,000 kDa, such as 1,500 to 15,000 kDa, including 2,000 to 10,000 kDa. Polysaccharide molecules in accordance with embodiments of the invention may have any configuration of branching and/or chain length while still preferentially binding to lymphatic tissue. Examples of polysaccharides of interest include, but are not limited to: pullulans, dextrins, dextran sulfates, dextrans, and the like. In certain embodiments, the polysaccharide is dextran, or a synthetic analogue thereof.

In some embodiments, a lymphatic tissue-specific dye may be conjugated to a detectable label. In certain embodiments, a detectable label may be a fluorescent dye, such as a physiologically-acceptable xanthene dye. Non-limiting examples of xanthene dyes include, e.g., fluoroscein, eosin and rhodamine dyes. The term "fluorescein dye" refers to a molecule that includes a fluorescein compound or a derivative thereof. Non-limiting examples of fluorescein dyes include fluorescein isothiocyanate (FITC), NHS-fluorescein, fluorescein-5-maleimide, and 5-iodoacetamido-fluorescein. The term "eosin dye" refers to a molecule that includes an eosin compound or a derivative thereof. Non-limiting examples of eosin dyes include eosin Y and eosin B. The term "rhodamine dye" refers to a molecule that includes a rhodamine compound or a derivative thereof. Non-limiting examples of rhodamine dyes include rhodamine B, rhodamine 6G, rhodamine 123, carboxytetramethylrhodamine (TAMRA), tetramethylrhodamine (TMR), and sulforhodamine 101 acid chloride (Texas Red).

Fluorescent dyes in accordance with embodiments of the invention may have any of a variety of absorbance and emission wavelength spectra to facilitate visualization of a lymphatic tissue. For example, a fluorescent dye in accordance with embodiments of the invention may have a maximum excitation wavelength or a maximum emission wavelength falling anywhere in the ultraviolet, visible light, and/or near infrared regions. In some embodiments, for example, a fluorescent dye may have a maximum excitation wavelength ranging from about 10 nm, up to about 25 nm, up to about 50 nm, up to about 75 nm, up to about 100 nm, up to about 125 nm, up to about 150 nm, up to about 175 nm, up to about 200 nm, up to about 225 nm, up to about 250 nm, up to about 275 nm, up to about 300 nm, up to about 325 nm, up to about 350 nm, up to about 375 nm, or up to about 400 nm, up to about 425 nm, up to about 450 nm, up to about 475 nm, up to about 500 nm, up to about 525 nm, up to about 550 nm, up to about 575 nm, up to about 600 nm, up to about 625 nm, up to about 650 nm, up to about 675 nm, up to about 700 nm, up to about 725 nm, up to about 750 nm, up to about 775 nm, up to about 800 nm, up to about 825 nm, up to about 850 nm, up to about 875 nm, up to about 900 nm, up to about 925 nm, up to about 950 nm, up to about 975 nm, or up to about 1,000 nm or more.

In some embodiments, a fluorescent dye may have a maximum emission wavelength ranging from about 10 nm, up to about 25 nm, up to about 50 nm, up to about 75 nm, up to about 100 nm, up to about 125 nm, up to about 150 nm, up to about 175 nm, up to about 200 nm, up to about 225 nm, up to about 250 nm, up to about 275 nm, up to about 300 nm, up to about 325 nm, up to about 350 nm, up to about 375 nm, or up to about 400 nm, up to about 425 nm, up to about 450 nm, up to about 475 nm, up to about 500 nm, up to about 525 nm, up to about 550 nm, up to about 575 nm, up to about 600 nm, up to about 625 nm, up to about 650 nm, up to about 675 nm, up to about 700 nm, up to about 725 nm, up to about 750 nm, up to about 775 nm, up to about 800 nm, up to about 825 nm, up to about 850 nm, up to about 875 nm, up to about 900 nm, up to about 925 nm, up to about 950 nm, up to about 975 nm, or up to about 1,000 nm or more.

In some embodiments, a detectable label may include a radioisotope. Non-limiting examples of radioisotopes include Calcium-47, Carbon-11, Carbon-14, Chromium-51, Cobalt-57, Cobalt-58, Erbium-169, Fluorine-18, Gallium-67, Gallium-68, Hydrogen-3, Indium-111, Iodine-123, Iodine-125, Iodine-131, Iron-59, Krypton-81m, Nitrogen-13, Oxygen-15, Phosphorus-32, Samarium-153, Selenium-75, Sodium-22, Sodium-24, Strontium-89, Technetium-99m, Thallium-201, Xenon-133, or Yttrium-90. Detection of radioisotopes can be conducted using standard methods, such as, e.g., positron emission tomography (PET), x-ray detection, fluoroscopy, or other imaging modalities to visualize a lymphatic tissue in a subject that has been contacted with a lymphatic tissue-specific dye that includes a radioisotope as a detectable label.

Covalent linking of a detectable label to a lymphatic tissue-specific dye can be accomplished via any of a variety of suitable techniques, such as, for example, by reacting a functional group (or portion thereof, e.g., a reactive moiety) on the detectable label with a functional group (or portion thereof, e.g., a reactive moiety) on the lymphatic tissue-specific dye in order to form a covalent bond. For example, a detectable label may be conjugated to a lymphatic tissue-specific dye using nucleophilic addition reactions that utilize nucleophilic moieties. Non-limiting examples of such reactions include reactions of sulfur nucleophiles, oxygen nucleophiles, carbon nucleophiles, or nitrogen nucleophiles with a suitable electrophile to form a covalent bond.

Subjects in accordance with embodiments of the invention generally include all mammals, including but not limited to, e.g., rodents (e.g., mice, rats, and rabbits), ungulates (e.g., sheep and cows), canines, felines, and primates (e.g., monkeys and humans). In some embodiments, subjects include transgenic animals. By "transgenic animal" is meant an animal whose genetic material has been altered using genetic engineering techniques.

Methods in accordance with embodiments of the invention may be carried out on a variety of regions of interest on a given subject where visualization of a lymphatic tissue is desirable. For example, in some embodiments, ocular tissue, e.g., a subject's eye or a portion thereof, may be used as the region of the subject where a lymphatic tissue is visualized. Specifically, in certain embodiments, a subject's cornea may be used as the region of the subject where a lymphatic tissue is visualized. In such embodiments, the fluorescently-labeled lymphatic tissue-specific dye may be, e.g., injected into the eye, (e.g., injected into an ocular tissue) or may be, e.g., injected into the subconjunctival space, in order to deliver the fluorescently-labeled lymphatic tissue-specific dye to the subject's eye, followed by visualization of a lymphatic tissue in the subject's eye or a portion thereof, e.g., in the subject's cornea. Visualizing a lymphatic tissue in a subject's cornea is desirable because the lymphatic tissue can be viewed in clear contrast against the background.

Contacting a region of a subject with a lymphatic tissue-specific dye may be accomplished using any of a variety of suitable techniques. In some embodiments, a lymphatic tissue-specific dye may be dissolved or suspended in a solution, e.g., an aqueous solution, at a suitable concentration before contacting the subject with the dye. In some embodiments, the concentration of the lymphatic tissue-specific dye in a solution ranges from 0.1% to 40% (w/v), such as 1% to 5% (w/v) and including 2.5% to 4% (w/v). The amount of the lymphatic tissue-specific dye that is used to contact the subject may vary depending on the particular region of the subject being contacted and the equipment being used. For example, in some embodiments, the subject is contacted with an amount ranging from 1 to 3,000 µL, such as 1 to 1,000 µL and including 3 to 300 µL. In certain embodiments, the subject is contacted with an appropriate volume of a solution having a defined concentration of the lymphatic tissue-specific dye so that the subject is contacted with the desired amount of the dye.

In certain embodiments, a lymphatic tissue-specific dye may be applied locally using suitable methods. For example, in some embodiments, a lymphatic tissue-specific dye may be topically applied to a region of a subject. Topical application can be accomplished by contacting the desired region of the subject with a suitable amount of, e.g., a composition that includes the lymphatic tissue-specific dye, such as, e.g., a solution (e.g., an aqueous solution), an ointment, or the like, having a suitable concentration of the lymphatic tissue-specific dye.

In some embodiments, a lymphatic tissue-specific dye may be administered to the subject via injection (e.g., via intradermal, subcutaneous, intramuscular, anterior chamber, intravitreal, or intravenous injection). In certain embodiments, a lymphatic tissue-specific dye may be injected directly into an anatomical structure of a subject and/or into a cavity or space within or around an anatomical structure of a subject. For example, in certain embodiments, a lymphatic tissue-specific dye may be injected into the subconjunctival space of a subject's eye. Injections may be carried out using suitable devices, such as, e.g., needles that are suitably sized to deliver a desired amount of the lymphatic tissue-specific dye to the region of the subject, as well as suitably sized syringes, intravenous fluid lines, intravenous fluid reservoirs, and the like.

In some embodiments, a lymphatic tissue-specific dye may be administered systemically to a subject. In such embodiments, the lymphatic tissue-specific dye may be administered, e.g., intravenously to the subject, or, e.g., via enteral administration to the subject (e.g., orally administered to the subject).

Following contacting the region of the subject with the lymphatic tissue-specific dye, aspects of the methods involve visualizing a lymphatic tissue in the region while the subject is still alive. By "visualizing lymphatic tissue" is meant creating one or more images of lymphatic tissue that can be viewed by an observer. In certain embodiments, visualizing the lymphatic tissue involves collecting one or more images of lymphatic tissue. For example, in some embodiments, a single image of a lymphatic tissue is collected at a particular point in time (i.e., a single time point). In some embodiments, a first image of a lymphatic tissue is collected at a first point in time, and a second image of the lymphatic tissue is collected at a second point in time. In such embodiments, the first and second images may be used to analyze changes in the lymphatic tissue that take place between the two points in time. In some embodiments, a time-course series of images is collected over a period of time to analyze changes in the lymphatic tissue that take place during the period of time. In some embodiments, a time-course series of images may include up to three, up to four, up to five, up to six, up to seven, up to eight, up to nine, or up to ten images taken over a period of time. In some embodiments, a time-course series of images may include up to 15, up to 20, up to 25, up to 30, up to 35, up to 40, up to 45, or up to 50 images or more.

A time-course series of images may be collected over a short period of time, over a long period of time, or over a combination of both short periods of time and long periods of time. By "short period of time" is meant an amount of time ranging from about 1 minute, up to about 5 minutes, up to about 10 minutes, up to about 15 minutes, up to about 20 minutes, up to about 25 minutes, up to about 30 minutes, up to about 45 minutes, up to about 1 hour, up to about 2 hours, up to about 3 hours, up to about 4 hours, up to about 5 hours, up to about 6 hours, up to about 7 hours, up to about 8 hours, up to about 9 hours, up to about 10 hours, up to about 15 hours, up to about 20 hours, or up to about 24 hours or more. By "long period of time" is meant an amount of time ranging from about 1 day (24 hours), up to about 2 days, up to about 3 days, up to about 4 days, up to about 5 days, up to about 6 days, up to about 7 days, up to about 8 days, up to about 9 days, up to about 10 days, up to about 12 days, up to about 15 days, up to about 20 days, up to about 25 days, or up to about 30 days or more, such as about one month or more, up to about 2 months or more, up to about 3 months or more, up to about 4 months or more, up to about 5 months or more, up to about 6 months or more, up to 1 year or more, up to 2 years or more, up to 3 years or more, up to 4 year or more, or up to 5 years or more.

In certain embodiments, a time-course series of images may be collected over a combination of one or more short periods of time as well as one or more long periods of time. For example, in some embodiments, a time-course series of images may include one or more images collected during a first short period of time, one or more images collected over a long period of time, and one or more images collected over a second short period of time. In some embodiments, a time-course series of images may include one or more images collected during a first long period of time, one or more images collected over a short period of time, and one or more images collected over a second long period of time. A time-course series of images in accordance with embodiments of the subject invention may include images taken over any of a variety of combinations of short and long periods of time.

In some embodiments, aspects of the subject methods involve visualizing lymphatic tissue in the region of the subject by collecting a time-lapse series of images of the region. A time-lapse series of images in accordance with embodiments of the invention may include a series of images taken at a designated frequency, wherein images are captured at a first rate, e.g., one image per second, and then played back at a faster rate, e.g., 10 images per second. In certain embodiments, a time-lapse series of images may be collected at a frequency ranging from about one image per second, up to about one image per hour, up to about one image per 5 hours, up to about one image per 10 hours, up to about one image per day, or a lower frequency.

In some embodiments, aspects of the subject methods involve visualizing lymphatic tissue in the region of the subject by collecting a video of the region. A video in accordance with embodiments of the invention includes a plurality of moving visual images that are stored on, e.g., a recording medium, such as a computer-readable medium.

Images collected in accordance with embodiments of the subject methods may have any of a variety of magnification levels and may include, e.g., low magnification images and/or high magnification images. Images collected in accordance with embodiments of the subject methods may also be collected along various axes of an optical system used to collect the images. The subject images and/or videos may also range in quality, and may include, e.g., high quality and/or low quality images.

In some embodiments, the subject methods involve visualizing lymphatic tissue, as described above, and simultaneously imaging other structures, including but not limited to blood vessels (e.g., arteries, capillaries, and/or veins, or portions thereof), nerves (e.g., axons and/or dendrites, or portions thereof), and/or other cells (e.g., inflammatory cells, immune cells, and the like) in the region of the subject that is being imaged. Structures other than lymphatic tissue can be visualized using any of a variety of suitable techniques, including, for example, using light microscopy to visualize blood inside vascular tissues, such as capillaries. In some embodiments, structures other than lymphatic tissue can be visualized using detectably-labeled compositions that bind to or interact with the tissue to be visualized, e.g., detectably-labeled antibodies that bind to the tissue being visualized, e.g., detectably-labeled antibodies that specifically bind to nerve tissue. Detectably-labeled compositions can be delivered to the desired region of the subject and visualized in the same ways as the lymphatic tissue-specific dye.

In some embodiments, the subject methods further involve inducing lymphangiogenesis (e.g., inducing inflammatory lymphangiogenesis) in a region of a subject. As used herein, the term "lymphangiogenesis" refers to the growth of new lymphatic vessels. Inducing lymphangiogenesis causes the growth of lymphatic vessels in the region of the subject, thus facilitating visualization of new and/or existing lymphatic tissue. Lymphangiogenesis may be induced using any of a variety of suitable techniques. For example, in certain embodiments, an inflammatory lymphangiogenesis protocol may be employed to stimulate lymphangiogenesis in the region of the subject where visualization of a lymphatic tissue is to take place. For example, in certain embodiments, a suture protocol may be used to induce lymphangiogenesis (e.g., inflammatory lymphangiogenesis) by placing a plurality of sutures in the region of the subject to cause suture-induced inflammatory neovascularization in the region, giving rise to inflammatory lymphangiogenesis. In some embodiments, penetrating keratoplasty (PKP), or corneal transplantation, is used to induce lymphangiogenesis in the region. PKP is accomplished by replacing at least a portion of the cornea with a donor cornea, thus stimulating inflammatory lymphangiogenesis in the subject. In some embodiments, micropocket implantation is used to induce lymphangiogenesis in the region. Micropocket implantation is accomplished by creating small pockets inside the corneal stroma to implant lymphangiogenesis-inducing agents, which agents are further described below.

In some embodiments, lymphangiogenesis may be induced by contacting the region of the subject with an agent that induces lymphangiogenesis. Non-limiting examples of lymphangiogenesis-inducing agents include: vascular endothelial growth factors (VEGFs) and isoforms thereof; platelet derived growth factor (PDGF) and isoforms thereof; tissue or cells (e.g., transplanted tissues or cells, such as tumor tissues or cells); and cell culture supernatant. In some embodiments, the subject methods involve contacting the subject with a candidate agent and evaluating the ability of the candidate agent to modulate one or more aspects of lymphatic tissue structure and/or function in a region of the subject. For example, in certain embodiments, the methods involve contacting the subject with a candidate agent and visualizing a lymphatic tissue in a region of the subject to evaluate, e.g., the ability of the candidate agent to stimulate or inhibit the proliferation of lymphatic tissue in the region of the subject. The methods can be used in a variety of pathological models, including, for example, models of inflammatory lymphangiogenesis, tissue injury and/or damage (e.g., trauma), tissue transplantation, infections, exposure to toxins, burns, and the like.

In some embodiments, transgenic animal models may be used to screen a candidate agent for use in modulating the structure and/or function of a lymphatic tissue. In some embodiments, a transgenic animal subject that is deficient in expression of a particular gene may be used in an assay to assess a candidate agent for the ability to modulate the structure and/or function of a lymphatic tissue. Such transgenic animals (e.g., transgenic mice) can also be used in any of a variety of pathological models, as described above.

Any of a variety of candidate agents can be screened for potential activity in the modulation of the structure and/or function of a lymphatic tissue in a subject. The term "candidate agent" as used herein is meant to include synthetic, naturally occurring, or recombinantly produced molecules (e.g., small molecule drugs; peptides; antibodies (including antigen-binding antibody fragments, e.g., to provide for passive immunity); endogenous factors present in eukaryotic or prokaryotic cells (e.g., polypeptides, plant extracts, and the like)); etc.). Of particular interest are screening assays for agents that have a low toxicity for human cells.

Candidate agents encompass numerous chemical classes, though typically they are organic molecules, preferably small organic compounds having a molecular weight of more than 50 and less than about 2,500 daltons. Candidate agents may be created synthetically or may be found among biomolecules including, but not limited to: peptides, saccharides, fatty acids, steroids, purines, pyrimidines, derivatives, structural analogs or combinations thereof.

Candidate agents can be obtained from a wide variety of sources, including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

A candidate agent can be administered to a subject in any manner desired and/or appropriate for delivery of the agent in order to examine the ability of the candidate agent to modulate the structure and/or function of a lymphatic tissue. For example, the candidate agent can be administered topically, by injection (e.g., by injection intravenously, intramuscularly, subcutaneously, and the like), orally, or by any other desirable means.

The methods can involve administering varying amounts of the candidate agent (from no agent to an amount of agent that approaches an upper limit of the amount that can be delivered successfully to the subject, e.g., within toxicity limits), and may include delivery of the agent in different formulations and routes of administration. Candidate agents can be administered singly or can be combined in combinations of two or more, especially where administration of a combination of candidate agents may result in a synergistic effect.

In some embodiments, the methods involve the administration of a therapeutic agent to the subject's eye (e.g., to the subject's ocular tissue) in order to evaluate the potential activity of the therapeutic agent in the modulation of the structure and/or function of a lymphatic tissue in the subject and/or treat the subject for a condition, e.g., a disease condition, of the eye. The term "therapeutic agent" as used herein is meant to include any composition administered to a patient for the purpose of treating a disease or condition related to aberrant functioning of the lymphatic system or the vascular system (e.g., the venous system).

Therapeutic agents that find use in the subject methods include, but are not limited to, agents that promote lymphangiogenesis and/or angiogenesis, as well as agents that inhibit lymphangiogenesis and/or angiogenesis. Non-limiting examples of therapeutic agents include: vascular endothelial growth factors (VEGFs) and isoforms thereof; vascular endothelial growth factor receptors (VEGF-Rs) and isoforms thereof; platelet derived growth factors (PDGFs) and isoforms thereof; histamines; antihistamines (e.g., antazoline sulfate, olopatadine); plasminogen activators; thrombospondins (e.g., thrombospondin-1); anti-inflammatories (e.g., betamethasone, dexamethasone, fluoromethalone, hydrocortisone acetate, prednisone); and non-steroidal anti-inflammatory drugs (e.g., diclofenac, ketorolac, flurbiprofen sodium, nepafenac) and the like.

In certain embodiments, a candidate agent or a therapeutic agent can be stably associated with, e.g., conjugated to, such as covalently bound to, a detectably-labeled lymphatic tissue-specific dye. Linking of the candidate agent or therapeutic agent to the lymphatic tissue-specific dye facilitates delivery of the agent directly to a lymphatic tissue. Covalent linking of an agent to a lymphatic tissue-specific dye can be accomplished via any of a variety of suitable techniques, such as, for example, by reacting a functional group (or portion thereof, e.g., a reactive moiety) on the agent with a functional group (or portion thereof, e.g., a reactive moiety) on the lymphatic tissue-specific dye in order to form a covalent bond. For example, an agent may be covalently-bound (e.g., conjugated, covalently linked) to a detectably-labeled lymphatic tissue-specific dye using nucleophilic addition reactions that utilize nucleophilic moieties. Non-limiting examples of such reactions include reactions of sulfur nucleophiles, oxygen nucleophiles, carbon nucleophiles, or nitrogen nucleophiles with a suitable electrophile to form a covalent bond.

The ability of a candidate agent or therapeutic agent to modulate the structure and/or function of a lymphatic tissue can be assessed by comparing two or more images obtained using the subject methods for visualizing a lymphatic tissue, as described herein. For example, an image obtained from a subject to whom the agent is administered can be compared to an image obtained from a control subject to whom the agent was not administered, and a comparison between the images can be used to determine, e.g., the extent of any modulation of the structure and/or function of the lymphatic tissue attributable to the agent.

In certain embodiments, aspects of the invention further include contacting the region of the subject with a lymphatic tissue-specific antibody, and visualizing the antibody in order to visualize further aspects of the lymphatic tissue. Lymphatic tissue-specific antibodies in accordance with aspects of the invention generally include those that specifically bind to proteins that are expressed exclusively or primarily on lymphatic tissues, such as, e.g., on lymphatic endothelial cells (LECs). Examples of lymphatic tissue-specific antibodies include, but are not limited to, anti-hyaluronan receptor (LYVE-1) antibodies, anti-vascular endothelial growth factor receptor-3 (VEGFR-3) antibodies, anti-Prospero-related homeobox-1 (Prox-1) antibodies, anti-podoplanin antibodies, anti-integrin alpha-9 antibodies, and anti-neuropilin-2 (NRP2) antibodies. Lymphatic tissue-specific antibodies can be conjugated to a detectable label and visualized as described above.

Image Detection Equipment

As summarized above, aspects of the invention involve collecting images of a tissue, e.g., a lymphatic tissue, in a region of a living subject that has been contacted with a fluorescently-labeled lymphatic tissue-specific dye. The subject images may be recorded using any of a variety of suitable image detection devices and associated equipment, including but not limited to, e.g., fluorescent microscopes, stereomicroscopes, confocal microscopes, ophthalmic slit-lamp microscopes, two-photon microscopes, and the like. In some embodiments, a single device is used to collect the subject images, whereas in other embodiments, a combination of two or more devices may be used to collect the subject images. Additional equipment that may be used to collect the subject images includes, but is not limited to: optical filters, optical light sources (e.g., bright field light sources, such as LED bright field light sources, fluorescent light sources, and the like) lenses, digital video cameras and related equipment, digital microscope cameras and related equipment; digital display systems and related equipment; and associated image processing and/or manipulation equipment, such as, e.g., a computer processor containing image processing and/or image manipulation software and/or capabilities that may be used to create, alter, enhance, display and/or reproduce one or more images and/or videos of a lymphatic tissue.

In some embodiments, the subject image detection equipment may be used to produce one or more images that contain a two-dimensional depiction of a lymphatic tissue, or a three-dimensional depiction of a lymphatic tissue. In certain embodiments, the subject image detection equipment may be used to create an image that contains a four-dimensional depiction of a lymphatic tissue, such as a video wherein a lymphatic tissue is depicted in a series of three dimensional images that change over time.

Aspects of the invention also include systems for use in carrying out the subject methods. Systems in accordance with embodiments of the invention may therefore include, e.g., a fluorescently-labeled lymphatic tissue-specific dye, and a device for detecting fluorescent light from a region of a living subject, as described above. In some embodiments, a device for detecting fluorescent light from a region of a living subject may include one or more components of the image detection equipment described herein. In certain embodiments, the subject systems may further include, e.g., a fluorescently-labeled lymphatic tissue-specific antibody.

Utility

The subject methods for visualizing a lymphatic tissue find use in a variety of applications, such as those discussed below.

The subject methods may be used to examine lymphatic processes induced by a wide array of pathological events or insults, such as, e.g., exposure to growth factors, infections, tumors, trauma, transplantation, or chemical burns. For example, in some embodiments, a first image of lymphatic tissue is taken from a region of a subject at a first point in time. After the image is taken, the subject is subjected to a stimulus, such as, e.g., administration of a growth factor. Following administration of the growth factor, another image of the lymphatic tissue is obtained and compared to the first image to determine the effect of the pathological event (e.g., contact with a growth factor) on the lymphatic tissue.

The subject methods may be used to study various molecular and cellular mechanisms underlying lymphatic formation, maturation, and regression. For example, the subject methods may be used in various transgenic or gene knock-out/knock-in animal models (e.g., transgenic mice) to examine the specific roles of certain molecular factors or pathways in various lymphatic processes. In some embodiments, for example, the methods involve presenting the same stimulus event, e.g., inducing inflammatory lymphangiogenesis, in both a transgenic animal subject and a wild type subject whose genetic material has not been altered. In some embodiments, the transgenic animal's genetic material has been altered so that the transgenic animal lacks one or more genes, e.g., one or more genes involved in the process of lymphangiogenesis that are present in a wild type animal. In some embodiments, the transgenic animal's genetic material has been altered so that the transgenic animal contains one or more genes that are not normally present, or are not normally expressed, in a wild type animal. Images of a lymphatic tissue are collected from both the wild type and the transgenic animals, and the images are compared to determine the effect of the alteration in the transgenic animal's genetic material on the response of the lymphatic tissue to the pathological event.

The subject methods may also be used in combination with other procedures (such as, e.g., bone marrow or specific cell type transplantation) to study the cellular origins of lymphatic endothelial cells. For example, the subject methods may be used to study whether and how bone marrow-derived cells, such as macrophages or monocytes, integrate into newly formed lymphatic vessels in the cornea during a certain period in an inflammatory response. In some embodiments, for example, a bone marrow transplantation procedure is conducted on a subject, wherein the transplanted bone marrow cells contain a detectable label, or a reporter gene that is not present in other cells within the subject. Following the bone marrow transplantation, a pathological insult, such as inflammatory lymphangiogeneis, is induced in a region of the subject to stimulate lymphangiogenesis in the region. As lymphangiogenesis progresses in the subject, images of the newly-formed lymphatic tissue are collected and the detectable label or reporter gene in the transplanted bone marrow cells is visualized to determine whether various cells in the newly-formed lymphatic tissue originated from the transplanted bone marrow.

The subject methods may be used to identify the similarities, differences, and interactions between blood and lymphatic vessels, which are two major circulatory networks in the body. The subject methods enable simultaneous observation of both vessel types at a molecular level. Their dynamic changes can be tracked over a short or long period of time in the same tissue and in the same subject. For example, in some embodiments, the methods involve inducing lymphangiogenesis and angiogenesis in a region of a subject, e.g., in the cornea of a subject. Imaging of the newly-formed lymphatic tissue is carried out using a lymphatic tissue-specific dye to obtain one or more images of the lymphatic tissue. Imaging of the newly-formed blood vessels is carried out using light microscopy to visualize blood in the blood vessels. The images of the lymphatic tissue and the blood vessels are then compared to determine the extent of interaction between the lymphatic tissue and the blood vessels, and to investigate similarities and differences between the development of the lymphatic tissue and the development of the blood vessels.

The subject methods may be used to investigate the interplay between lymphatic vessels and other cellular and nerve components in the local tissue environment. For example, transgenic animal strains with specific fluorescent reporter genes, such as, e.g., CD11c YFP mice, IFN-γ YFP mice, macrophage CFP mice, and thy1 YFP mice can be used in combination with the subject methods to visualize the interaction of lymphatic tissue with other cellular and nerve components of a local tissue environment. For example, in some embodiments, the methods involve inducing lymphangiogenesis in a region of a subject, e.g., in the cornea of a subject. Imaging of the newly-formed lymphatic tissue is carried out using a lymphatic tissue-specific dye to obtain one or more images of the lymphatic tissue. Imaging of the other cellular and/or nerve components is carried out by visualizing the specific fluorescent reporter gene product using, e.g., fluorescent imaging equipment, as described above. The images are then analyzed to determine the extent of interaction between the lymphatic tissue and the other cellular and/or nerve components, and to investigate similarities and differences between the development of the lymphatic tissue and the development and/or infiltration of the other cellular and/or nerve components into the region of the subject.

The subject methods may be used to test the effect of a biological or a pharmaceutical manipulation (e.g., to test the effect of a candidate agent, or, e.g., to test the effect of a therapeutic agent) on various dynamic lymphatic processes (from early formation to late regression). Such data may be used to determine how and when a biological or pharmaceutical manipulation should be conducted in order to maximize a beneficial therapeutic outcome for a lymphatic disorder. For example, in some embodiments, the ability of a candidate agent or a therapeutic agent to modulate a dynamic lymphatic process can be assessed by comparing two or more images obtained using the subject methods for visualizing a lymphatic tissue, as described herein. For example, in some embodiments, a pathological event (e.g., inflammatory lymphangiogenesis) is presented to two different subjects. One subject is administered a candidate agent or a therapeutic agent at a first point in time (e.g., shortly after inflammatory lymphangiogenesis is induced in the subjects) and the other subject is administered the same agent at a second, different point in time (e.g., a long period of time after lymphangiogenesis is induced in the subjects). One or more images obtained from the first subject are then compared to one or more images obtained from the second subject to determine, e.g., the impact of the timing of the administration of the agent on the dynamic lymphatic process in the subjects.

In certain embodiments, a subject may be administered a therapeutic agent or a candidate agent that has been covalently linked to a detectably-labeled lymphatic tissue-specific dye. Covalently linking the candidate agent or therapeutic agent to the lymphatic tissue-specific dye facilitates delivery of the agent directly to a lymphatic tissue, e.g., facilitates targeted delivery of the agent to a lymphatic tissue. Visualization of a lymphatic tissue in the subject can then be used to determine the effectiveness of the targeted delivery of the agent as compared to, e.g., systemic delivery of the agent, or local, non-targeted delivery of the agent. For example, in some embodiments, a pathological event (e.g., inflammatory lymphangiogenesis) is presented to two different subjects. One subject is administered a therapeutic agent (e.g., a therapeutic agent that is not covalently linked to another molecule), and the other subject is administered the same therapeutic agent covalently linked to a detectably-labeled lymphatic tissue-specific dye. Lymphatic tissue in the subjects is then visualized using the subject methods. One or more images obtained from the first subject are compared to one or more images obtained from the second subject (and/or a control subject to whom the therapeutic agent was not administered) to determine, e.g., the impact of the targeted delivery of the therapeutic agent on a dynamic lymphatic process in the subjects.

In some embodiments, the methods can be used to monitor the progress of a therapeutic composition in the treatment of a disease or condition. For example, in some embodiments, a subject with a disease or condition is administered a lymphatic tissue-specific dye, as described herein, and an image of the subject's lymphatic tissue is obtained. The subject is then administered a course of therapy, e.g., the subject is administered a pharmaceutical composition for a specified period of time. Following administration of the pharmaceutical composition, the subject is again administered a lymphatic tissue-specific dye and another image of the subject's lymphatic tissue is obtained. The first image and the second image of the subject's lymphatic tissue are then compared to determine the effect of the pharmaceutical composition on the structure and/or function of the subject's lymphatic tissue.

The subject methods may also be used to generally characterize lymphatic dysfunction in human subjects. Lymphatic dysfunction has been found in many human eye diseases. The subject methods can be used to directly visualize and monitor lymphatic vessels in human eyes and provide first-hand and real-time information for disease diagnosis, evaluation, and therapeutic intervention. For example, in some embodiments, a human subject is administered a lymphatic tissue-specific dye that includes a detectable label, e.g., a FITC label. The lymphatic tissue-specific dye is injected into the human subject's eye, e.g., into the subconjunctival space, and the dye contacts lymphatic tissue in the human subject's eye. A caregiver (e.g., a physician or nurse) then collects images of the lymphatic tissue and the images are analyzed to determine, e.g., whether the structure and/or function of the lymphatic tissue indicates that the human subject is suffering from a disease or condition.

The subject methods may be used to directly observe lymphatic vessels in the cornea of a human subject, and the observations can be extrapolated to characterize the condition of lymphatic vasculatures in other tissues in general. The behavior of lymphatic vessels in the eye of a subject is indicative of the behavior of lymphatic vessels throughout the entire body of the subject. As such, eye examinations, such as fundus microscopy and retinal fluorescent angiography, are commonly performed to screen and monitor systemic diseases, such as diabetes, hypertension, and arterial sclerosis. The subject methods therefore find use in diagnosing these and other diseases and/or disorders, including but not limited to, e.g., lymphedema, inflammation, transplant rejection, diabetes, diabetic retinopathy, age-related macular degeneration (AMD), and choroidal neovascularization (CNV). For example, in some embodiments, a human subject is administered a lymphatic tissue-specific dye that includes a detectable label, e.g., a FITC label. The lymphatic tissue-specific dye is injected into the human subject's eye, e.g., into the subconjunctival space, and the dye contacts lymphatic tissue in the human subject's eye. A caregiver (e.g., a physician or nurse) then collects images of the lymphatic tissue and the images are analyzed to determine, e.g., whether the structure and/or function of the lymphatic tissue indicates that the human subject is suffering from a systemic disease or condition. The result of the examination is then used to diagnose the subject with the systemic disease or condition.

As summarized in Table 1, below, compared to conventional ex vivo visualization methods, such as immunohistochemistry techniques, the subject methods provide a number of novel features and advantages. For example, the subject methods allow for time-course tracking of dynamic lymphatic processes in the same tissue over a short or long period of time. The subject methods may be used to produce highly reliable information on lymphatic vessels in their natural morphology, state, and interactions with the local environment. Both time-lapse images and real time videos can be taken from low to high magnification and along various axes for data analysis.

TABLE 1

Advantages of the subject methods over conventional ex vivo immunohistochemical microscopic assay techniques

|  | Conventional ex vivo tissue sample assay | In vivo live imaging technique of the subject methods |
|---|---|---|
| Sample/Subject | Dead tissues | Live animal or patient |
| Number of animals sacrificed for multiple time point studies | Large | No sacrifice needed |
| Examination of lymphatic vessels in their natural state, location, and interaction with the environment | No | Yes |
| Longitudinal tracking of dynamic lymphatic processes in the same tissue or subject | No | Yes |
| Four-dimensional imaging of lymphatic vessels | No | Yes |
| Real-time evaluation of the effect of a pharmaceutical or biological intervention | No | Yes |
| Application to human and clinical studies | No | Yes |

Figure 2:
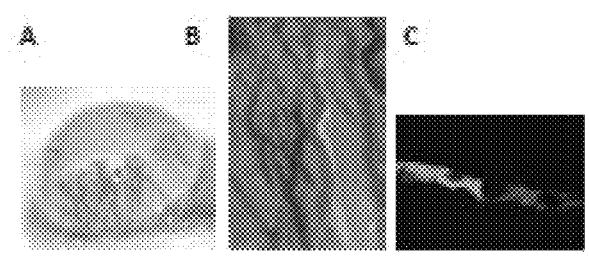
FIG. 2 illustrates a comparison between slit-lamp microscopy (Panel A) and an embodiment of the subject visualization methodology (Panel B). Panel A: a low magnification view of blood vessels obtained by slit-lamp microscopy. Panel B: both blood and lymphatic vessels are clearly revealed using the subject methods. Panel C: a close-up view of lymphatic endothelial cells at the cellular level.
Figure 3:
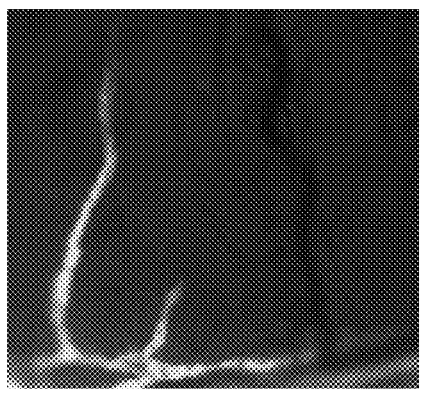
FIG. 3 illustrates live imaging of corneal lymphatic vessels that are labeled in different fluorescent colors and are induced by different models or pathological insults. Panel A: Lymphatic vessels labeled with FITC-dextran (green) and induced by micropocket implantation of a lymphatic-inducing ligand, VEGF-C. Panel B: Lymphatic vessels labeled with rhodamine-dextran (red) and induced by suture placement.
Figure 3:

Compared with existing ophthalmic slit-lamp microscopy, which is widely used in both laboratory and clinical settings, the subject methods demonstrate several major advantages. Slit-lamp microscopy is greatly limited by technical issues and fails to generate high quality images with details. Moreover, it can only detect blood vessels, not lymphatic vessels (FIG. 2, Panel A). In contrast, the subject methods facilitate direct observation of both blood and lymphatic vessels at high resolution and with contrast against the background (FIG. 2, Panel B and Panel C). The subject methods may be used to generate images reaching a resolution of, e.g., 0.5 microns, and can detect lymphatic vessels at the cellular level. Even lymphatic vessels in close proximity can be clearly visualized and distinguished from each other. Since both vessel types (blood vessels and lymphatic vessels) can be evaluated in the same tissue over a long period of time, the subject methods provide an excellent tool for identifying the similarities, disparities, and interactions between these two vascular systems. Since the subject lymphatic tissue-specific large molecular weight dextran can be labeled with a wide array of detectable labels, such as FITC (green) and rhodamine (red), the subject methods can be used to visualize corneal lymphatic vessels in different colors, as desired (FIG. 3).

The following examples are offered by way of illustration and not by way of limitation.

EXPERIMENTAL

I. Materials and Methods
A. Animals
Normal adult male BALB/c mice (Taconic Farms, Germantown, N.Y.) were used for the experiments. All mice were treated according to ARVO Statement for the Use of Animals in Ophthalmic and Vision Research, and the protocols were approved by the Animal Care and Use Committee, University of California, Berkeley. Mice were anesthetized using a mixture of ketamine, xylazine, and acepromazine (50 mg, 10 mg, and 1 mg/kg body weight, respectively) for each surgical procedure.

B. Induction of Corneal Inflammatory Lymphangiogenesis and Hemangiogenesis by Suture Placement
A suture-induced inflammatory neovascularization model was used. Briefly, 3 to 8 sutures (11-0 nylon, AROSurgical, Newport Beach, Calif.) were placed into the corneal stroma without penetrating into the anterior chamber, followed by application of antibiotic ointment.

C. Induction of Corneal Lymphangiogenesis by Micropocket Implantation
Slow-releasing pellets of vascular endothelial growth factor-C (VEGF-C) were implanted into a micropocket surgically created in central corneal stroma (1.0 mm apart from the limbal vascular arcade) using a Von Graefe knife, followed by application of antibiotic ophthalmic ointment.

D. Ophthalmic Slit-Lamp Microscopic Examination of Corneal Blood Vessels
Eyes were examined by an ophthalmic slit-lamp microscope with an integrated digital camera system (SL-D4 and DC-3; Topcon Medical Systems, Japan) before and 14 days after suture placement.

E. Non-Contact Live Imaging and Videos of Corneal Blood and Lymphatic Vessels with Fluorescent Stereomicroscopes
Mice were anesthetized and kept warm with an isothermal pad (Braintree Scientific, Braintree, Mass.) throughout the imaging process. Large molecular weight FITC- or rhodamine-labeled dextran (2,000 kDa molecular weight) was injected into the subconjunctival space with the assistance of an adjustable eye and head holder. Dye uptake was continuously monitored under a fluorescent stereomicroscope connected to a camera and a computer station with imaging software and a display screen. Digital images were taken under two light exposure conditions: FITC excitation light alone or combined with LED bright field light. A series of time-lapse images were taken under both FITC excitation light and LED bright field light sources using a Leica M165F FC stereomicroscope (JH Technology, San Jose, Calif.) in a time frame of 3 images per second. A total of 120 images taken within 40 seconds were streamed with the NIH Image J software.

F. Live Imaging of Lymphatic Vessels in the Skin

The experiment was performed similarly as described above except that the FITC-labeled dextran dye was injected intradermally into the skin at the tail tip of the subject. Digital images were taken to demonstrate the cross-sections of lymphatic vasculatures in the skin.

G. Live Imaging and Videos of the Cornea with the Advanced Two-Photon Excitation Fluorescence Microscope A custom-built two-photon microscope based on the Movable Objective Microscope (Sutter Instrument Co., CA) was used. The microscope was enclosed in a Faraday cage to minimize electrical noise and stray light. The live subject (a mouse) was positioned on a portable platform with a feedback-regulated heating pad and an adjustable eye and head holder. The excitation laser pulses were focused onto the cornea by a high numerical-aperture, water-immersion objective. Fluorescence emission was collected with a GaAsP photomultiplier tube behind an optical filter. The objective was controlled by a micromanipulator allowing translation in x-y-z axes for fine micron-scale spatial resolution. The system can reach a z-resolution of 0.5 microns. Large field-of-view images were taken with an air objective. The entire system was driven by the ScanImage software developed at Janelia Farm, and fluorescence images were assigned pseudo-colors.

Two-photon videos were taken and streamed with the NIH Image J software. For one of the videos, a stack of 100 image slices, each an average of 3 frames, was taken with a z-step of 10 µm. For another video, 70 image frames were acquired with a z-step of 1 µm with no averaging. One of the videos was generated with a z-step of 0.5 µm.

H. Pharmaceutical Interventions

Mice were randomized to receive systemic administrations of anti-VEGFR-2 monoclonal antibodies (800 µg; DC101; ImClone Systems Corporation, wholly-owned subsidiary of Eli Lilly and Company, New York, N.Y.) or their isotype controls on Day 0 and Day 3 after 4 suture placement.

II. Results

A. Example 1: Visualization of Lymphatic Vessels in the Cornea of a Subject

To induce inflammatory lymphangiogenesis and hemangiogenesis in the cornea, a suture protocol was employed, as described above. Corneal lymphatic vessels were visualized by subconjunctival injection of large molecular weight fluorescein isothiocyanate (FITC)-labeled dextran. The dye uptake was continuously monitored under a custom-built live imaging system with an adjustable eye and head holder to secure steady pictures while the mouse was breathing. Two types of live imaging systems were tested: 1) a non-contact live imaging system with a fluorescent stereomicroscope, and 2) a more advanced live imaging system with a two-photon excitation microscope. As demonstrated in FIG. 1, while the non-contact system was able to produce high quality images (Panels A-D, F) and a video without touching the cornea, the highly advanced two-photon system yielded more depth-sectioning and cellular details of the tissue and vessels in the images collected (Panel E) as well as several videos. A time-lapse two-photon video was taken, showing a newly formed lymphatic network in the corneal stroma. The video was taken at low magnification along the central-to-peripheral axis. Another two-photon live video was taken showing depth-sectioning details of stromal lymphatic vessels lying behind the epithelial cell layer of the cornea. The video was taken at high magnification along the superficial-to-deep axis. Another two-photon live video was taken at high magnification showing that two nearby lymphatic vessels appeared to be overlapping from the top view, but were located at different layers if viewed from the side.

The subject imaging methods were sensitive enough to detect lymphatic vessels at various stages, which differ greatly in shapes and degrees of complexity, as illustrated in FIG. 1, Panel A. A wide range of lymphatic morphologies was visualized, whether they pertained to the early stages of budding and branching, the middle stages of bridging and networking, or the late stage of regressing. The foot prints (arrow in FIG. 1, Panel A) of the almost regressed lymphatic vessels were also detectable under higher magnification.

The subject imaging methods demonstrated great advantages over conventional ex vivo immunohistochemical assay techniques. One serious limitation to the ex vivo assay is that the method is not applicable for time-course evaluation of the same tissue. Previously, to appreciate a glimpse of lymphatic transformation over a certain period of time, a large number of animals had to be sacrificed at different time points for extensive ex vivo assays on dead tissues. The entire process was time, labor, and resource demanding, and was also fraught with inaccurate information. Using the subject methods, the same cornea was followed for a short or a long period of time and dynamic lymphatic changes in the same tissue were examined during the early phase of lymphatic formation, or the late phase of lymphatic regression. As demonstrated in FIG. 1, Panel B, it was observed that within a period of 48 hours in the progression phase, an inflammatory lymphatic vessel had developed from a single stem into an elaborated network (FIG. 1, Panel B, upper two images). Lymphatic regression, however, occurred more gradually and it took about 2 months for a complex network to become minimal residues, as shown in a long-term 4-month study (FIG. 1, Panel B, middle two and lower two images).

B. Example 2: Visualization of Both Lymphatic Vessels and Blood Vessels in the Cornea of a Subject Since blood and lymphatic vessels often accompany each other, and it is important to evaluate both structures in many studies, the advantage of the subject methods over ophthalmic slit-lamp microscopy, which is commonly used in both research laboratories and clinics, was demonstrated. As demonstrated in FIG. 1, Panel C, while only blood vessels (arrow) were detectable by slit-lamp microscopy (left two images), both blood (arrowheads) and lymphatic vessels (arrows) were clearly revealed by the subject methods (right two images). While blood vessels appeared in dark shadows under the FITC fluorescence excitation source alone, they showed up in their natural red color under the combined light sources in an LED bright field view. Moreover, the images obtained by the subject methods were of better resolution and quality. The FITC-dextran labeled vessels in live corneas expressed LYVE-1, the lymphatic specific marker (data not shown). Since the subject methods enable simultaneous observation and tracking of both vessel types, the subject methods offer an excellent platform for identifying the similarities and disparities between the two vascular systems in response to a stimulus. For example, although not a focus of this study, it was noted that inflamed lymphatic vessels regressed earlier than blood vessels within live cornea (arrowheads in FIG. 1, Panel A and B), as seen previously with immunohistochemistry methods.

C. Example 3: Advantages of Live Imaging of Lymphatic Vessels in the Cornea Over Other Non-Transparent Tissues, Such as the Skin The advantages of live imaging of lymphatic vessels in the cornea over other non-transparent tissues, such as the skin, which is normally endowed with lymphatic vessels, were demonstrated. As shown in FIG. 1, Panel D, live imaging of tail skin, a site used for lymphatic imaging in previous studies, revealed a cross-sectional view of the lymphatics, which was obscured by a layer of body hairs (FIG. 1, Panel D, upper image). In contrast, imaging within the cornea, a transparent tissue that is free of any pre-existing or background vessels, showed an entire tree of newly formed lymphatic vessels from their peripheral roots to central branches (FIG. 1, Panel D, middle image). This method also enabled the observation of the lymphatic vessels in the context of their local and physiological environment, which also harbored newly formed blood vessels and the site of pathological stimulation. Terminal lymphatics (FIG. 1, Panel D, middle image, arrowheads) encircling a suture spot (FIG. 1, Panel D, middle image, arrow) were observed. More dynamic biological events, such as rapid red blood cell circulation (FIG. 1, Panel D, lower image, arrow) within blood vessels, were also detected. A time-lapse video was also obtained, showing terminal lymphatics surrounding a suture spot. Rapid red blood cell flow was also observed inside nearby blood vessels.

D. Example 4: Live Imaging of the Cornea of a Subject Using a Two-Photon Excitation Fluorescence Microscope To obtain more details of the cornea at a cellular level, live imaging with a custom-built and highly advanced two-photon excitation fluorescence microscope was performed. The system reached a z-resolution of 0.5 microns with the high numerical aperture objective and allowed for a precise evaluation of the most delicate features of the lymphatic vessels within the live cornea. As illustrated in FIG. 1, Panel E, detailed structures of the cornea were revealed showing well-organized epithelial cells in top layers (FIG. 1, Panel E, upper two images) and newly formed lymphatic vessels in the stroma (FIG. 1, Panel E, middle two and lower two images). This delicate system also enabled precise positioning of lymphatic vessels in close proximity. As shown in FIG. 1, Panel E, lower two images, it was found that two lymphatic vessels appeared to cross over each other from the top view (FIG. 1, Panel E, lower left image) were indeed located at different layers when viewed from a side view (FIG. 1, Panel E, lower right image). The ultra-structural information was recorded in multi-dimensional time-lapse videos, which were taken under low to high magnifications and along various axes. A time-lapse two-photon video was taken, showing a newly formed lymphatic network in the corneal stroma. The video was taken at low magnification along the central-to-peripheral axis. Another two-photon live video was taken showing depth-sectioning details of stromal lymphatic vessels lying behind the epithelial cell layer of the cornea. The video was taken at high magnification along the superficial-to-deep axis. Another two-photon live video was taken at high magnification showing that two nearby lymphatic vessels appeared to be overlapping from the top view, but were located at different layers if viewed from the side.

E. Example 5: Effect of Systemically Administered Vascular Endothelial Growth Factor Receptor-2 (VEGFR-2) Neutralizing Antibodies on Inflammatory Lymphangiogenesis within Live Corneas To demonstrate an application of the subject methods in the evaluation of a pharmacological intervention in inflammatory lymphangiogenesis, a longitudinal study on the consequences of systemic administrations of vascular endothelial growth factor receptor-2 (VEGFR-2) neutralizing antibodies on inflammatory lymphangiogenesis within live corneas was performed. As shown in FIG. 1, Panel F, a brief treatment regimen with two injections at Day 0 and Day 3 after the suture placement had led to a significant reduction of lymphatic growth in both density and length. These data provide the first in vivo imaging evidence showing that VEGFR-2 is critically involved in inflammatory lymphangiogenesis in the cornea.

F. Example 6: Visualization of Lymphatic Vessels Induced by Different Insults and in Different Fluorescent Colors To further demonstrate that corneal lymphatic vessels can be induced by various pathological insults and can be visualized by lymphatic dyes having detectable labels of various fluorescent colors, experiments were performed using both suture placement and corneal micropocket implantation models. The micropocket implantation assay has been widely used for lymphatic and blood vessel research in various fields. The implanted pellet contained VEGF-C, which is known to be involved in lymphangiogenesis and cancer metastasis. Newly formed lymphtic vessels in the cornea were labeled via subconjunctival injection of 2,000 kDa molecular weight dextran labeled with either FITC or rhodamine. As shown in FIG. 3, Panel A, VEGF-C implantation induced lymphatic vessel formation into the cornea, which was labeled by FITC-dextran (green). Additionally, the lymphatic vessels induced by suture placement were also detected by rhodamine-dextran (red) labeling.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for visualizing lymphatic tissue in an ocular region of a living subject, the method comprising:
    contacting the ocular region with a detectably-labeled lymphatic tissue-specific dye via injection into a subconjunctival space; and
    detecting the labeled dye to visualize lymphatic tissue in the ocular region of the living subject;
    wherein the detectably-labeled lymphatic tissue-specific dye comprises a fluorescent label covalently bound to a physiologically-acceptable polysaccharide.

2. The method according to claim 1, wherein the ocular region is the cornea.

3. The method according to claim 1, wherein the method comprises inducing lymphangiogenesis in the ocular region.

4. The method according to claim 3, wherein the ocular region is the cornea and lymphangiogenesis is induced in the cornea using a suture protocol, an implantation protocol or a transplantation protocol.

5. The method according to claim 1, wherein the polysaccharide has a molecular weight ranging from 1,000 kDa up to 10,000 kDa.

6. The method according to claim 5, wherein the polysaccharide is dextran.

7. The method according to claim 1, wherein the detecting comprises obtaining an image at a single time.

8. The method according to claim 1, wherein the detecting comprises obtaining two or more images at different times.

9. The method according to claim 1, wherein the detecting comprises obtaining a video over a period of time.

10. The method according to claim 1, wherein the method further comprises visualizing blood vessels in the ocular region.

11. The method according to claim 1, wherein the method further comprises contacting the ocular region with a candidate agent and evaluating the impact of the candidate agent on at least one of lymphatic and blood vessel activity in the ocular region.

12. The method according to claim 11, wherein the candidate agent is covalently bound to the detectably-labeled lymphatic tissue-specific dye.

13. The method according to claim 1, wherein the method further comprises contacting the ocular region with a therapeutic agent conjugated to the detectably-labeled lymphatic tissue-specific dye.

14. The method according to claim 1, wherein the method further comprises contacting the ocular region with a detectably-labeled lymphatic tissue-specific antibody and detecting the antibody.

15. The method according to claim 14, wherein the detectably-labeled lymphatic tissue-specific dye comprises a fluorescent label having a first maximum emission wavelength, and the detectably-labeled lymphatic tissue-specific antibody comprises a fluorescent label having a second maximum emission wavelength that is different from the first maximum emission wavelength.

16. The method according to claim 1, wherein the living subject is a mammal.

17. The method according to claim 1, wherein the polysaccharide is selected from a pullulan, a dextrin, a dextran sulfate, and a dextran.

18. The method according to claim 17, wherein the fluorescent label comprises a physiologically-acceptable xanthene dye.

19. The method according to claim 18, wherein the fluorescent label is selected from a fluorescein dye and a rhodamine dye.

20. The method according to claim 19, wherein the polysaccharide is dextran.

21. The method according to claim 1, wherein the method for visualizing lymphatic tissue consists essentially of:
    contacting the cornea with a detectably-labeled lymphatic tissue-specific dye that comprises a fluorescent label covalently bound to a physiologically-acceptable polysaccharide having a molecular weight ranging from 1,000 kDa up to 10,000 kDa; and
    detecting the labeled dye to visualize lymphatic tissue in the cornea of the living subject.

22. The method according to claim 21, wherein the polysaccharide is selected from a pullulan, a dextrin, a dextran sulfate and a dextran.

23. The method according to claim 22, wherein the polysaccharide is dextran.

* * * * *